United States Patent
Eom et al.

(10) Patent No.: US 9,382,575 B2
(45) Date of Patent: Jul. 5, 2016

(54) BIOMOLECULE DETECTION APPARATUS INCLUDING PLURALITY OF ELECTRODES

(75) Inventors: Kun-sun Eom, Seoul (KR); Dong-ho Lee, Seongnam-si (KR); Jeo-young Shim, Yongin-si (KR); Hee-jeong Jeong, Seoul (KR); Tae-han Jeon, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 608 days.

(21) Appl. No.: 13/614,881

(22) Filed: Sep. 13, 2012

(65) Prior Publication Data
US 2013/0264206 A1    Oct. 10, 2013

(30) Foreign Application Priority Data
Apr. 9, 2012 (KR) .................. 10-2012-0036802

(51) Int. Cl.
  *C12Q 1/68* (2006.01)
  *G01N 33/487* (2006.01)

(52) U.S. Cl.
  CPC ............ *C12Q 1/68* (2013.01); *G01N 33/48721* (2013.01)

(58) Field of Classification Search
  CPC . G01N 27/447; G01N 27/453; G01N 33/487; Y10S 977/852; Y10S 977/733; Y10S 977/72; Y10S 977/721; C12Q 1/68
  See application file for complete search history.

(56) References Cited

U.S. PATENT DOCUMENTS

| | | | |
|---|---|---|---|
| 6,015,714 A | 1/2000 | Baldarelli et al. | |
| 6,362,002 B1 | 3/2002 | Denison et al. | |
| 6,428,959 B1 | 8/2002 | Deamer | |
| 7,638,034 B2 | 12/2009 | Sansinena et al. | |
| 7,731,826 B2 * | 6/2010 | Hibbs et al. | 204/450 |
| 9,250,202 B2 | 2/2016 | Chun | |
| 2007/0020146 A1 * | 1/2007 | Young et al. | 422/82.01 |
| 2010/0066348 A1 * | 3/2010 | Merz et al. | 324/71.1 |
| 2010/0289505 A1 * | 11/2010 | Zhang | 324/663 |
| 2010/0292101 A1 * | 11/2010 | So | C12Q 1/6869 506/16 |
| 2010/0327847 A1 * | 12/2010 | Leiber et al. | 324/71.1 |
| 2011/0155574 A1 | 6/2011 | Golovchenko et al. | |
| 2011/0162963 A1 | 7/2011 | Hibbs et al. | |
| 2011/0168562 A1 | 7/2011 | Nuckolls et al. | |
| 2011/0224098 A1 | 9/2011 | Luan et al. | |
| 2011/0226623 A1 | 9/2011 | Timp et al. | |
| 2012/0103821 A1 * | 5/2012 | Harrer et al. | 205/84 |
| 2012/0193231 A1 * | 8/2012 | Afzali-Ardakani et al. | 204/451 |
| 2012/0193263 A1 * | 8/2012 | Felix | 206/521 |
| 2012/0267729 A1 * | 10/2012 | Dang et al. | 257/414 |
| 2012/0322055 A1 * | 12/2012 | Royyuru | 435/6.1 |
| 2013/0037410 A1 * | 2/2013 | Xu et al. | 204/601 |

FOREIGN PATENT DOCUMENTS

| | | |
|---|---|---|
| KR | 10-0730350 B1 | 4/2007 |
| WO | WO 2011-142614 A2 | 11/2011 |
| WO | WO2012065480 | * 5/2012 |

* cited by examiner

*Primary Examiner* — Jennifer Dieterle
(74) *Attorney, Agent, or Firm* — Leydig, Voit & Mayer, Ltd.

(57) ABSTRACT

A biomolecule detection apparatus comprising a nanopore device having a front surface and rear surface and including a nanopore having a nano-sized diameter; a reservoir disposed adjacent to a rear surface of the nanopore device; and a power supply unit comprising a first electrode disposed in a front of the nanopore device; a second electrode disposed inside the reservoir; and a third electrode disposed adjacent the nanopore and between the first electrode and the second electrode; as well as a method of using the biomolecule detection apparatus to detect a biomolecule in a sample.

23 Claims, 7 Drawing Sheets

US 9,382,575 B2

BIOMOLECULE DETECTION APPARATUS INCLUDING PLURALITY OF ELECTRODES

CROSS-REFERENCE TO RELATED APPLICATIONS

This application claims the benefit of Korean Patent Application No. 10-2012-0036802, filed on Apr. 9, 2012, in the Korean Intellectual Property Office, the disclosure of which is incorporated herein in its entirety by reference.

BACKGROUND

A variety of methods have been developed to detect target biomolecules, like deoxyribonucleic acids (DNA), in a sample. Among these methods, a nanopore method has been spotlighted in conjunction with a high-sensitivity DNA detection system. A variety of DNA detection systems using nanopores have been published to date. For example, a base sequence of DNA may be determined or it may be determined whether DNA is single stranded or double stranded by detecting a slight change in a current that occurs when DNA translocates through a nanopore.

Such DNA detection systems using nanopores enable DNA to translocate through a fine nanopore formed through a thin layer by moving DNA toward the fine nanopore according to an electrophoresis phenomenon. For example, if a sample liquid solution including DNA is filled in a front end of the nanopore, and voltages are applied to the front and rear of the nanopore, DNA having negative charge moves toward an anode. Thus, DNA may translocate through the nanopore by placing a cathode in the sample liquid solution in the front of the nanopore and the anode in a reservoir in the rear of the nanopore.

However, although a strong electrolyte having good ion conductivity is used as a liquid solution, since an ion translocation area is rapidly reduced in the nanopore, resistance greatly increases, which causes a voltage drop near the nanopore. As a result, an electric field formed between the anode and the cathode is mainly distributed near the nanopore. Thus, DNA are merely spread by a thermal motion in the sample liquid solution in the front end of the nanopore having a weak electric field, and then are induced to the nanopore if the DNA reach a limited region near the nanopore in which the electric field having an intensity that is higher than a predetermined level is distributed.

SUMMARY

Provided is a biomolecule detection apparatus including additional electrodes near a nanopore so as to easily induce a target biomolecule toward the nanopore.

Additional aspects will be set forth in part in the description which follows and, in part, will be apparent from the description, or may be learned by practice of the presented embodiments.

According to an aspect of the present invention, a biomolecule detection apparatus is provided, comprising a nanopore device having a front surface and rear surface and including a nanopore having a nano-sized diameter; a reservoir disposed adjacent to a rear surface of the nanopore device; and a power supply unit comprising a first electrode positioned in front of the nanopore device; a second electrode disposed inside the reservoir, wherein the nanopore device is positioned between the first and second electrodes; and a third electrode disposed adjacent to the nanopore between the first electrode and the second electrode.

A sample liquid solution containing target biomolecules may be deposited on the front surface of the nanopore device, and the nanopore may be formed vertically so as to connect the front and the rear surfaces of the nanopore device so that the target biomolecules pass through the nanopore into the reservoir. The reservoir may be configured to contain the target biomolecules and an electrolyte passing through the nanopore.

The first electrode may be position to contact and be electrically connected to the sample liquid solution deposited on the front surface of the nanopore device, and the second electrode may be disposed to contact and be electrically connected to the electrolyte contained in the reservoir.

The first electrode may have a negative electric potential or is grounded, and the second electrode and the third electrode have positive electric potentials.

A difference in the electric potential between the first electrode and the second electrode may be greater than that between the first electrode and the third electrode.

The third electrode may be attached to the front of the nanopore device around the entrance of the nanopore, and may be in a shape of a ring surrounding the nanopore.

The third electrode may be disposed facing the front of the nanopore device and separated by a space around the entrance of the nanopore, for instance, a space of less than about 10 μm.

Alternatively, the third electrode may be disposed inside the nanopore. In one embodiment, the nanopore device may include a bottom substrate providing the rear side (rear surface) thereof and a top substrate providing the front side (front surface) thereof, and the third electrode may be disposed between the bottom substrate and the top substrate and exposed through an inner wall of the nanopore.

The power supply unit may further include: a fourth electrode disposed between the first electrode and the third electrode.

The third electrode or the fourth electrode may include a plurality of electrode layers having the same electric potential or different electric potentials.

A difference in the electric potential between the first electrode and the third electrode may be greater than that between the first electrode and the fourth electrode, and a difference in the electric potential between the first electrode and the second electrode may be greater than that between the first electrode and the third electrode.

The power supply unit may further include: a fourth electrode disposed facing the third electrode with respect to the nanopore.

The nanopore device may further include a nanochannel having a diameter greater than the nanopore.

The nanochannel may be disposed on the same axis as the nanopore and extends in an axial direction from the nanopore.

The nanochannel may be disposed perpendicularly extending from the nanopore.

The third electrode may be attached to the front of the nanopore device around the entrance of the nanopore or may be disposed facing the front of the nanopore device and separated by a space.

The nanopore device may include a bottom substrate including the nanopore and a top substrate including the nanochannel, and the third electrode may be disposed between the bottom substrate and the top substrate.

The third electrode may be disposed inside the nanochannel and may be exposed to the outside through an inner wall of the nanochannel.

The third electrode may be attached onto a top surface of the nanochannel or may be disposed facing the top surface of the nanochannel and separated by a space.

The power supply unit may further include: a fourth electrode disposed around the entrance of the nanochannel between the first electrode and the third electrode.

The fourth electrode may be attached onto the top surface of the nanochannel, may be disposed facing the top surface of the nanochannel and separated by a space, or may be disposed inside the nanochannel.

A difference in the electric potential between the first electrode and the third electrode may be greater than that between the first electrode and the fourth electrode, and a difference in the electric potential between the first electrode and the second electrode may be greater than that between the first electrode and the third electrode.

The power supply unit may further include: a fourth electrode disposed facing the third electrode with respect to the nanopore.

The third electrode and/or the fourth electrode may be disposed in the front of the nanopore device or inside the nanopore.

Also provided is a method of detecting a biomolecule using the biomolecule detection apparatus. The method may comprise applying a sample containing a target biomolecule to the front surface of the biomolecule detection apparatus of claim 1; applying an electric field to the nanopore of the biomolecule detection apparatus, whereby the target biomolecule is transported through the nanopore of the biomolecule detection apparatus; and sensing a change in current between the electrodes of the biomolecule detection device, wherein a change in current indicates the passage of the target biomolecule through the nanopore. The electric field is applied, for instance, by supplying a current to the electrodes by way of the power supply unit.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
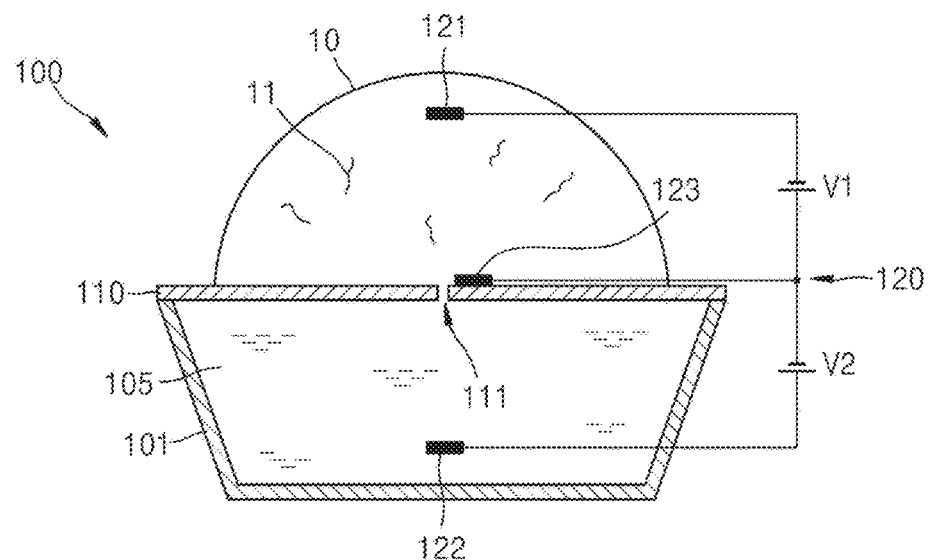
FIG. 1 is a schematic conceptual view of a structure of a biomolecule detection apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

FIG. 1 is a conceptual view schematically illustrating a structure of a biomolecule detection apparatus 100 according to an embodiment.

Referring to FIG. 1, the biomolecule detection apparatus 100 according to the present embodiment may include a nanopore device 110 having a front and rear surfaces and including a nanopore 111 having a nano-sized diameter, a reservoir 101 for containing a sample and an electrolyte 105 that passes through the nanopore 111, and a power supply unit 120 for forming an electric field near the nanopore 111 to move target biomolecules 11. For example, a diameter of the nanopore 111 may be 100 nm or less, preferably 10 nm or less, especially about 5 nm.

The nanopore 111 may be formed by vertically penetrating between the front and rear surfaces of the nanopore device 110 and connected to the reservoir, thereby forming a passageway from the front surface of the nanopore device into the reservoir. By way of illustration, the nanopore may have a diameter of, for example, approximately 5 nm. When in use, a sample liquid solution 10 including the target biomolecules 11, for example, deoxyribonucleic acid (DNA), may be deposited on the front surface of the nanopore device 110 so as to cover the nanopore 111. Although the sample liquid solution 10 having a large size is shown in FIG. 1 for illustrative convenience, the sample liquid solution 10 may be disposed on the nanopore device 110 in the form of a small droplet.

The reservoir 101 may be disposed adjacent to the rear surface of the nanopore device 110, and contain the electrolyte 105 through which a current is likely to flow. The nanopore is connected to the reservoir and, when the reservoir is filled with electrolyte solution, the solution may also occupy the nanopore. The electrolyte 105 may be the same type as the sample liquid solution 10. For example, the electrolyte 105 may be a conductive solution such as a KCl solution. The target biomolecules 11 included in the sample liquid solution 10 deposited on the front surface of the nanopore device 110 may be contained in the reservoir 101 after passing through the nanopore 110.

The power supply unit 120 may include a first electrode 121 disposed in front of the nanopore device 110 and positioned so as to contact and be electrically connected to a sample liquid solution 10 deposited on the front surface of the nanopore device 110. In other words, the first electrode is positioned in the biomolecule detection apparatus at a distance from the front surface of the nanopore device. The power supply unit 120 also may include a second electrode 122 disposed in the reservoir 101 in the rear of the nanopore device 110, and positioned so as to contact and be electrically connected to an electrolyte 105 solution contained in the reservoir. Thus, the nanopore device is positioned between the first and second electrodes. The power supply unit may further comprise a third electrode 123 located between the first electrode 121 and the second electrode 122. The third electrode 123 should be located adjacent to the nanopore 111, or within the nanopore 111.

In a case where the target biomolecules 11 have negative charges like DNA, the first electrode 121 may have a negative electric potential or be grounded, and the second electrode 122 and the third electrode 123 may have positive electric potentials. In a case where the target biomolecules 11 have positive charges, polarities may be opposite each other. For example, the second electrode 122 may have the negative electric potential or be grounded, the third electrode 123 may have the negative electric potential, and the first electrode 121 may have the positive electric potential. In FIG. 1, a negative voltage is applied to the first electrode 121, and positive voltages are applied to the second electrode 122 and the third electrode 123. In this regard, an electric potential difference V1+V2 between the first electrode 121 and the second electrode 122 may be greater than the electric potential difference V1 between the first electrode 121 and the third electrode 123.

If a voltage is applied to each of the first, second, and third electrodes 121, 122, and 123, the target biomolecules 11 contained in the sample liquid solution 10 disposed in the front of the nanopore device 110 move toward the second electrode 122 according to an electric force. Then, the target biomolecules 11 pass through the nanopore 111 and are contained in the reservoir 101. For example, the target biomolecules 11 may pass through the narrow nanopore 111 one by one. When the target biomolecules 11 pass through the nanopore 111, a small change in a current occurs between the first electrode 121 and the second electrode 122. It may, therefore, be possible to detect and analyze the target biomolecules 11 by sensing the change in the current. Alternatively, although not shown, the target biomolecules 11 passing through the nanopore 111 may be detected by using two separate electrodes facing each other with respect to the nanopore 111.

Figure 2:
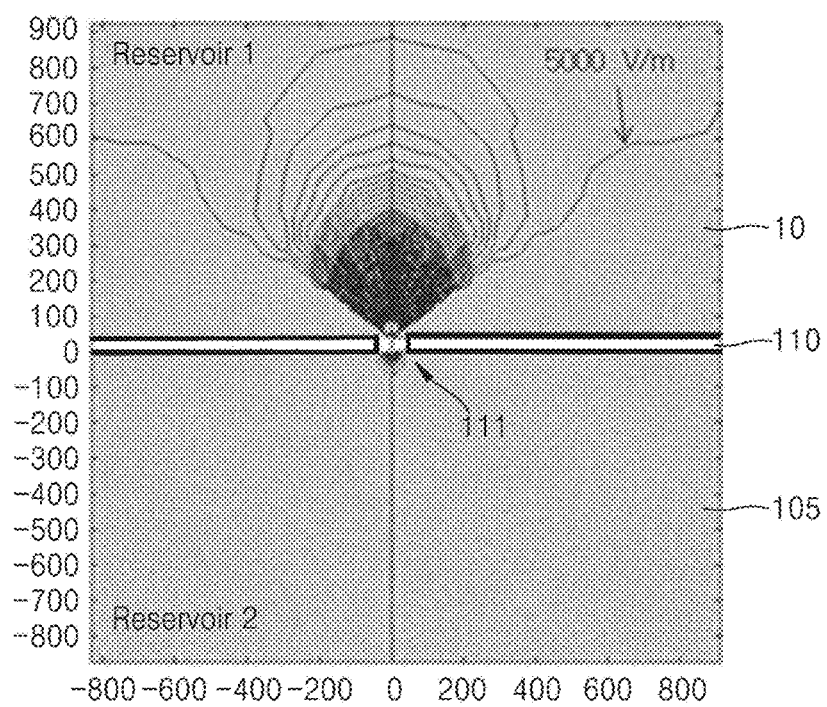
FIG. 2 is an exemplary diagram of a distribution of an electric field in a case where an additional electrode is disposed near a nanopore.
Figure 3:
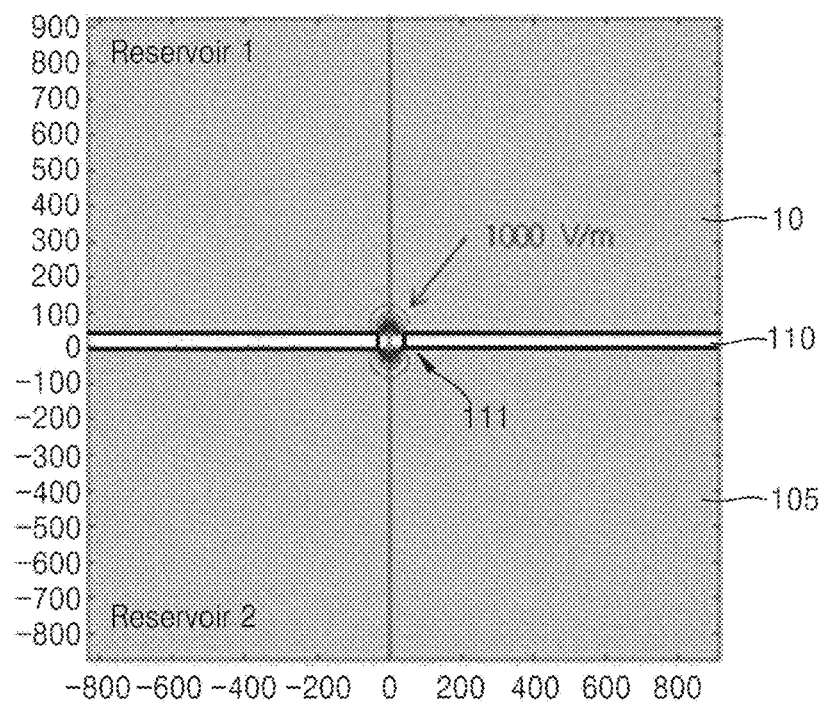
FIG. 3 is an exemplary diagram of a distribution of an electric field in a case where no additional electrode is disposed near a nanopore.

According to the present embodiment, the target biomolecules 11 may more easily move because of the third electrode 123 disposed in proximity to the entrance of the nanopore 111. For example, FIG. 2 is an exemplary diagram of a distribution of an electric field in a case where the third electrode 123 is additionally disposed near the nanopore 111, and FIG. 3 is an exemplary diagram of a distribution of an electric field in a case where the third electrode 123 is not disposed near the nanopore 111. For illustrative convenience, the distributions of electric fields of FIGS. 2 and 3 are provided based on the assumption that the sample liquid solution 10 and the electrolyte 105 are disposed in a shape of a cylinder in the front and rear of the nanopore device 110.

Referring to FIG. 3, in the case where the third electrode 123 is not disposed near the nanopore 111, when voltages are applied to the first electrode 121 and the second electrode 122, a voltage drop mostly occurs in the nanopore 111, and the distribution of the electric field that is a distance differential of the voltage drop focuses around the nanopore 111. Whereas, referring to FIG. 2, in the case where the third electrode 123 is additionally disposed near the nanopore 11, a voltage drop of V1 occurs between the first electrode 121 and the third electrode 123, and thus the electric field having an intensity higher than a predetermined level is distributed over a wide range of the sample liquid solution 10. Meanwhile, in the electrolyte 105 between the third electrode 123 and the second electrode 122, the voltage drop mostly occurs in the nanopore 111 and thus the electric field focuses near the nanopore 111.

For example, in FIG. 3, an electric field having an intensity higher than about 1000 V/m in the front of the nanopore 111 is distributed in a range of a volume of a sphere having a diameter of about 100 nm, whereas, in FIG. 2, the electric field having an intensity higher than about 5000 V/m is distributed in a whole range of the sample liquid solution 10. Thus, in FIG. 3, the target biomolecules 11 are merely spread within the sample liquid solution 10 by a thermal motion before reaching a small sphere region having a diameter of about 100 nm near the nanopore 111. However, in FIG. 2, the electric field having an intensity higher than a predetermined level is distributed in a wide range of the sample liquid solution 10, and thus the target biomolecules 11 are easily induced to the nanopore 111.

To distribute the electric field over the wide range of the sample liquid solution 10 as described above, the third electrode 123 may be disposed in the front of the nanopore device 110 so that the third electrode 123 is closer to the sample liquid solution 10 than the electrolyte 105 in the reservoir with respect to the nanopore device 110. For example, the third electrode 123 may be attached to the front of the nanopore device 110 or may be disposed facing apart from the front of the nanopore device 110 by a predetermined gap.

Figure 4A:
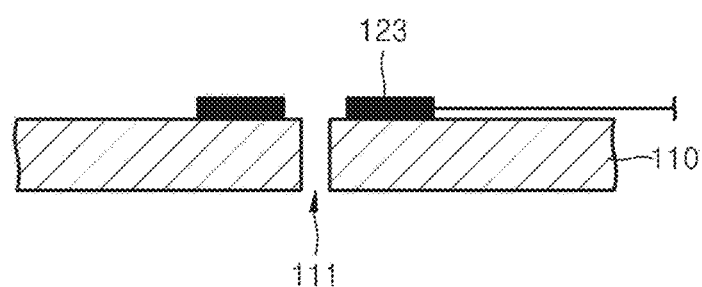
FIGS. 4A and 4B are schematic cross-sectional and plan views of an exemplary shape of an additional electrode attached to the front of a nanopore device, respectively.
Figure 4B:
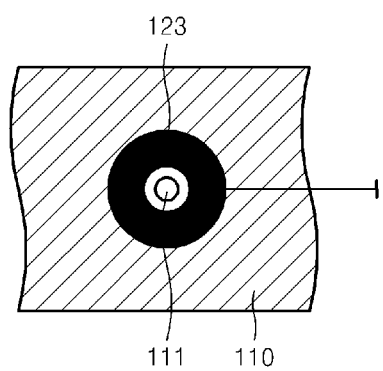

FIGS. 4A and 4B are schematic cross-sectional and plan views of an exemplary shape of the third electrode 123 additionally attached to the front of the nanopore device 110, respectively.

Referring to the cross-sectional view of FIG. 4A, the third electrode 123 may be attached to the front of the nanopore device 110 near the nanopore 111. Although the third electrode 123 may be disposed on one side of the nanopore 111, as shown in FIG. 4A, the third electrode 123 may be disposed on both sides of the nanopore 111 or may be disposed wholly surrounding the nanopore 111. For example, as shown in the plan view of FIG. 4B, the third electrode 123 may be in a ring shape and may surround the nanopore 111.

Figure 5:
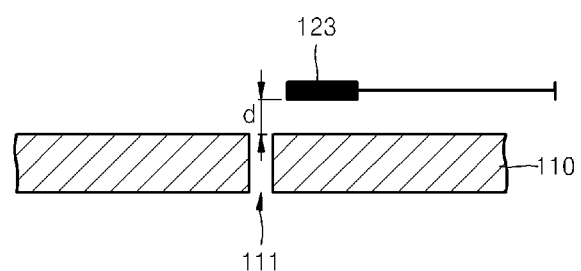
FIG. 5 is a schematic cross-sectional view of an exemplary additional electrode disposed facing the front of a nanopore device and separated by a space according to an embodiment.

Referring to FIG. 5, the third electrode 123 may be disposed facing the nanopore device 110 and separated by the space d away from the front thereof around the nanopore 111. If the space d between the third electrode 123 and the nanopore device 110 is too large, an electric field may be focused on the nanopore 111 in a space between the third electrode 123 and the nanopore 111. Thus, the space d between the third electrode 123 and the nanopore device 110 should be less than about 10 μm.

Figure 6:
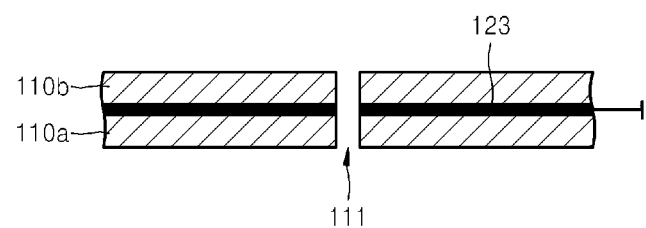
FIG. 6 is a schematic cross-sectional view of another exemplary additional electrode disposed inside a nanopore according to an embodiment.

The third electrode 123 may be disposed inside the nanopore 111. FIG. 6 is a schematic cross-sectional view of the third electrode 123 disposed inside the nanopore 111. Referring to FIG. 6, the third electrode 123 is disposed inside the nanopore 111 and is exposed through an inner wall thereof. In this case, the nanopore device 110 may include a bottom substrate 110a providing the rear side (rear surface) of the nanopore device, and a top substrate 110b providing the front side (front surface) of the nanopore device. The third electrode 123 may be formed by using a metal layer disposed between the bottom substrate 110a and the top substrate 110b. By way of example, the nanopore device 110 of FIG. 6 may be manufactured by depositing a metal layer (e.g., third electrode) on the bottom substrate 110a, and then forming the top substrate 110b on the metal layer.

As described in the various embodiments above, a third electrode 123 is disposed near the nanopore 111 in the biomolecule detection apparatus 100, inducing charged particles or biomolecules to move toward the nanopore 111. In these embodiments, an electric field is distributed over a wide range of the sample liquid solution 10 due to a voltage drop between the first electrode 121 and the third electrode 123, and thus charged target biomolecules 11 contained in the sample liquid solution 10 are not induced to the nanopore 111 through diffusion by a thermal motion, but may be induced to the nanopore 111 by the electric field. As such, since the target biomolecules 11 may be easily induced, an electrolyte having relatively low density (for example, densities of the target biomolecules 11) may be used as the sample liquid solution 10, which reduces noise generated by high density, thereby achieving more precise detection. Also, the voltage V1 between the first electrode 121 and the third electrode 123 and the voltage V2 between the third electrode 123 and the second electrode 122 are appropriately distributed, thereby preventing various problems from occurring due to an extremely high voltage.

Figure 7:
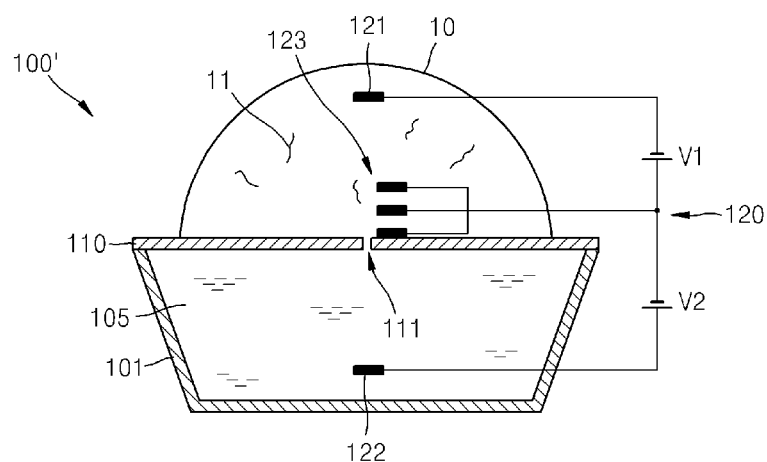
FIG. 7 is a schematic conceptual view of a structure of a biomolecule detection apparatus according to an embodiment.

FIG. 7 is a schematic conceptual view of a structure of a biomolecule detection apparatus 100' according to another embodiment.

In the biomolecule detection apparatus 100' of FIG. 7, the third electrode 123 may include a plurality of electrode layers. For example, the third electrode 123 may include two or more electrode layers arranged in a vertical axis inside the sample liquid solution 10. The plurality of electrode layers are arranged inside the sample liquid solution 10, thereby further increasing a distribution of an electric field in the sample liquid solution 10. In some instances, the plurality of electrode layers have the same electric potential. In other instances, the power supply unit 120 may be configured to generate a small difference in the electric potential between the electrode layers. For example, a difference in the electric potential between the electrode layers of the third electrode 123 may be smaller than that between the first electrode 121 and the third electrode 123. The construction of the biomolecule detection apparatus 100', except for the construction of the third electrode 123, is the same as that of the biomolecule detection apparatus 100 of FIG. 1.

Furthermore, two or more additional electrodes may be disposed between the first electrode 121 and the second electrode 122. For example, the biomolecule detection apparatus 100" of FIG. 8 further includes a fourth electrode 124. The fourth electrode 124 may be disposed between the first electrode 121 and the third electrode 123 in a vertical axis direction inside the sample liquid solution 10. In such a construction, when an electric potential of the first electrode 121 is 0, an electric potential of the fourth electrode 124 is V1, an electric potential of the third electrode 123 is V1+V2, and an electric potential of the second electrode 122 is V1+V2+V3, which may steadily increase. That is, a difference in the electric potential between the first electrode 121 and the third electrode 123 may be greater than that between the first electrode 121 and the fourth electrode 124, and a difference in the electric potential between the first electrode 121 and the second electrode 122 may be further greater than that between the first electrode 121 and the third electrode 123. Accordingly, a relatively uniform voltage drop occurs between the first electrode 121 and the fourth electrode 124 and between the fourth electrode 124 and the third electrode 123, and thus an electric field may be uniformly distributed over a wide range of the sample liquid solution 10. Thus, the target biomolecules 11 included in the sample liquid solution 10 may be more easily induced to the nanopore 111. Meanwhile, a structure of the third electrode 123 including the plurality of electrode layers of FIG. 7 may apply the fourth electrode 124 of FIG. 8. That is, the fourth electrode 124 may include a plurality of electrode layers.

Figure 8:
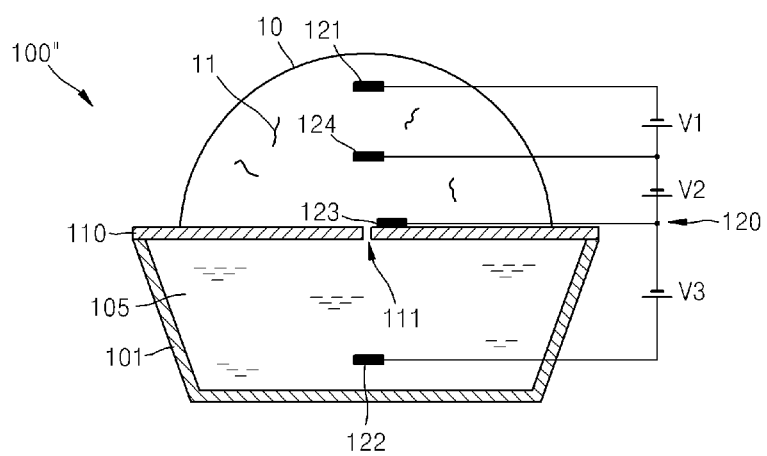
FIG. 8 is a schematic conceptual view of a structure of a biomolecule detection apparatus according to an embodiment.
Figure 9:
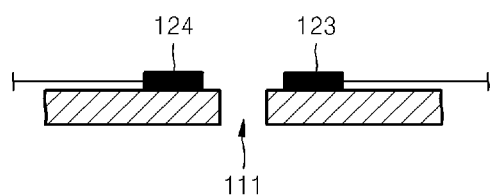
FIG. 9 is a schematic cross-sectional view of an exemplary arrangement of additional electrodes of FIG. 8.

Although the fourth electrode 124 is disposed between the first electrode 121 and the third electrode 123 in FIG. 8, the fourth electrode 124 may be disposed facing the third electrode 123 with respect to the nanopore 111. For example, as shown in FIG. 9, the third electrode 123 and the fourth electrode 124 may be disposed in the front of the nanopore device 110 with respect to the nanopore 111. Alternatively, similar to the embodiment described in FIG. 6, the third electrode 123 and the fourth electrode 124 may be disposed inside the nanopore 111. In this alternative, the third electrode 123 and the forth electrode 124 may be arranged so as to face each other.

Although the third electrode 123 and the fourth electrode 124 are shown in FIGS. 8 and 9, three or more additional electrodes may be disposed between the first electrode 121 and the second electrode 122 in some embodiments. In the case of using a plurality of additional electrodes, when the target biomolecules 11 contained in the sample liquid solution 10 pass through the nanopore 111, a minor change in a current or a voltage may occur between the third electrode 123 and the fourth electrode 124. Thus, such a change in the current or the voltage between the third electrode 123 and the fourth electrode 124 is sensed, thereby detecting the target biomolecules 11. A distance between the third electrode 123 and the fourth electrode 124 is shorter than that between the first electrode 121 and the second electrode 122, and thus the change in the current or the voltage between the third electrode 123 and the fourth electrode 124 may be more precisely sensed than a change in the current or the voltage between the first electrode 121 and the second electrode 122.

Figure 10:
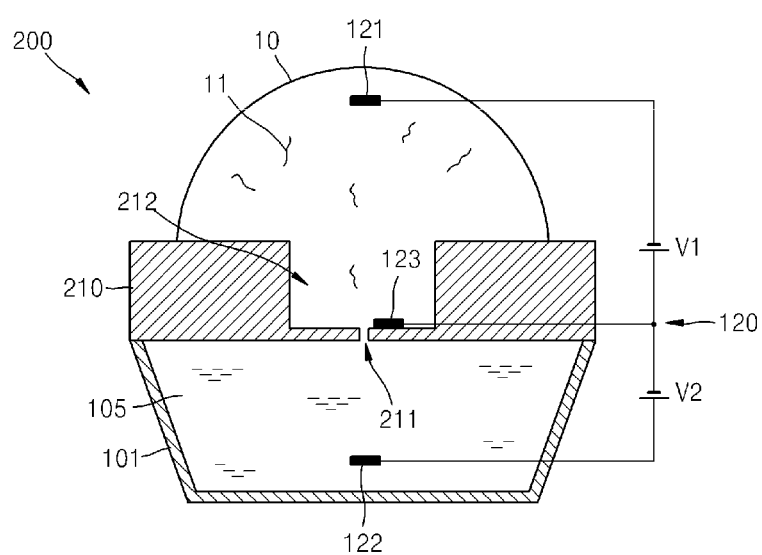
FIG. 10 is a schematic conceptual view of a structure of a biomolecule detection apparatus according to an embodiment.

FIG. 10 is a schematic conceptual view of a structure of a biomolecule detection apparatus 200 according to another embodiment.

Referring to FIG. 10, the biomolecule detection apparatus 200 according to the present embodiment may include a nanopore device 210 including a nanopore 211 having a nano-sized diameter and a nanochannel 212 having a diameter greater than the nanopore 211, the reservoir 101 for containing a sample and the electrolyte 105 that pass through the nanopore 211, and the power supply unit 120 for forming an electric field near the nanopore 211 to move the target biomolecules 11. The biomolecule detection apparatus 200 of FIG. 10 is different from the biomolecule detection apparatus 100 of FIG. 1 in that the biomolecule detection apparatus 200 includes the nanochannel 212. The other construction and operation of the biomolecule detection apparatus 200 is the same as described with reference to the biomolecule detection apparatus 100 of FIG. 1.

The nanochannel 212 may be disposed on the same axis as the nanopore 211, and extend in an axial direction from the nanopore 211. In this structure, a direction in which the target biomolecules 11, e.g., DNA, move in the nanochannel 212 is the same as that in which the target biomolecules 11 pass through the nanopore 211. The target biomolecules 11 contained in the sample liquid solution 10 are induced by an electric field to pass through the nanochannel 212 (having the diameter greater than the nanopore 211), and then to pass through the nanopore 211. For example, the diameter of the nanochannel 212 may be between about 5 nm and about 500 nm. In some embodiments, a filler may be disposed in the nanochannel 212 in order to mediate the speed at which the target biomolecules 11 travel, e.g., prevent speeds becoming too great. Additionally, the filler may allow target biomolecules 11 that are randomly twisted in various shapes, like DNA, to uniformly unfold into straight shapes while the target molecules 11 move. The filler may be any material that reduces the speed of translocation of the target biomolecule through the nanochannel, such as a gel.

In FIG. 10, a voltage drop does not just occur in the nanopore 211 but also occurs in the nanochannel 212, and thus the electric field may be further distributed by the nanochannel 212. That is, in addition to the reinforced voltage drop due to the first electrode 121 and the third electrode 123, the voltage drop due to the nanochannel 212 may allow the electric field to be more effectively distributed in a whole region of the sample liquid solution 10.

Similar to other embodiments described above, the third electrode 123 may be attached to the front of the nanopore device 210 around the nanopore 211, may be disposed facing the front of the nanopore device 210 and separated by a predetermined space, or may be disposed inside the nanopore 211. Furthermore, in the present embodiment, the third electrode 123 may be disposed near a top surface 213 of the nanochannel 212. For example, the third electrode 123 may be attached onto the top surface 213 of the nanochannel 212 or may be disposed facing the top surface 213 of the nanochannel 212 and separated by the predetermined space.

Figure 11:
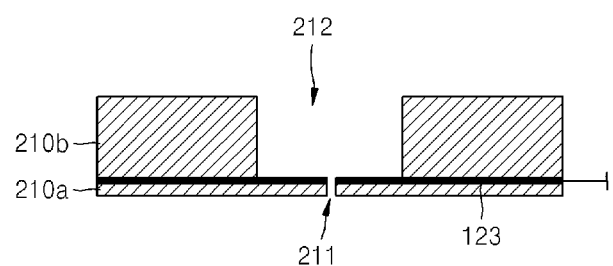
FIG. 11 is a cross-sectional view of an exemplary arrangement of an additional electrode according to an embodiment.

In a case where the third electrode 123 is attached to the front of the nanopore device 210 near the nanopore 211, as shown in FIG. 11, the nanopore device 210 may include a bottom substrate 210a including the nanopore 211 and a top substrate 210b including the nanochannel 212. The third electrode 123 may be disposed between the bottom substrate 210a and the top substrate 210b. For example, the third electrode 123 may be formed by forming the bottom substrate 210a, including the nanopore 211, and depositing a metal layer on a surface of the bottom substrate 210a. Thereafter, the top substrate 210b, including the nanochannel 212, may be formed on the third electrode 123.

Although not shown, in a case where the third electrode 123 is disposed facing the front of the nanopore device 210 near the nanopore 211 and separated by a predetermined space, the bottom substrate 210a may be formed to further include a lower part of the nanochannel 212. Meanwhile, the top substrate 210b may be formed to further include an upper part of the nanochannel 212. In this case, the third electrode 123 between the bottom substrate 210a and the top substrate 210b is disposed inside the nanochannel 212 and is exposed to the outside through an inner wall of the nanochannel 212.

Figure 12:
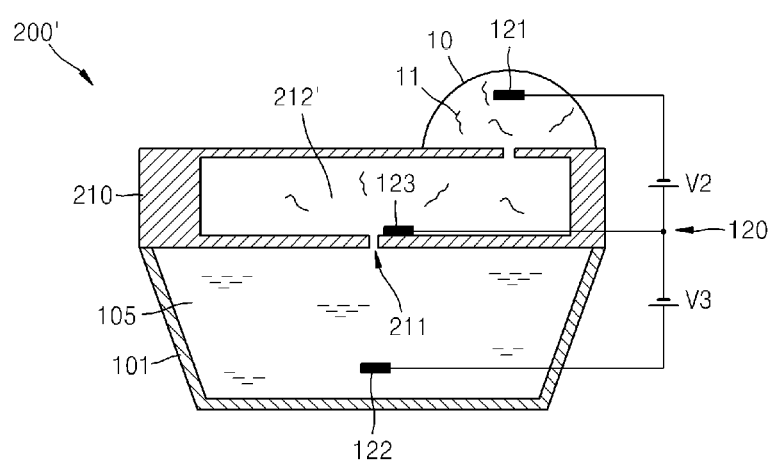
FIG. 12 is a schematic conceptual view of a structure of a biomolecule detection apparatus according to an embodiment.

Although the nanochannel 212 extends in the axial direction from the nanopore 211 along the same axis as the nanopore 211 in the biomolecule detection apparatus 200 of FIG. 10, the present embodiment is not limited thereto. Referring to FIG. 12, a biomolecule detection apparatus 200' according to another embodiment may include a nanochannel 212' perpendicularly connected to the nanopore 211. In the embodiment of FIG. 12, the nanochannel 212' is disposed in a horizontal direction perpendicular to the axial direction of the nanopore 211. Thus, a direction (i.e., a horizontal axial direction) in which the target biomolecules 11, e.g., DNA, move in the nanochannel 212' is perpendicular to a direction (i.e. a vertical axial direction) in which the target biomolecules 11 pass through the nanopore 211. Other features of the biomolecule detection apparatus 200' of FIG. 12 may be the same as that of the biomolecule detection apparatus 200 of FIG. 10.

Figure 13:
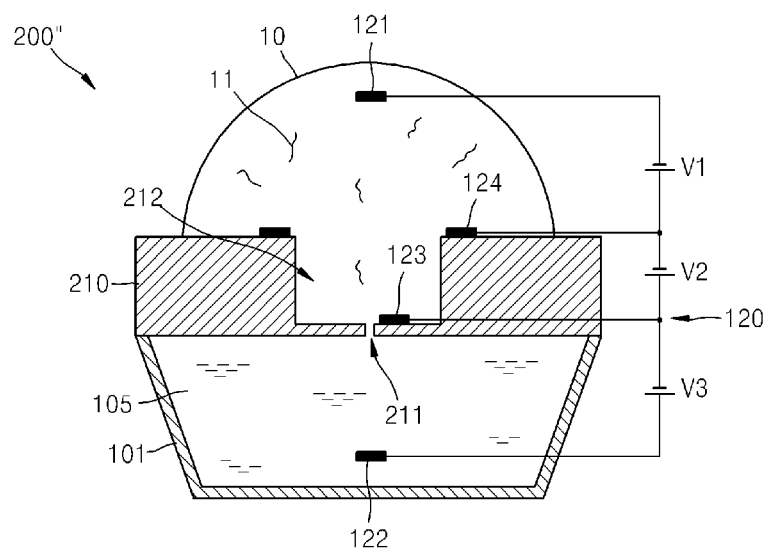
FIG. 13 is a schematic conceptual view of a structure of a biomolecule detection apparatus according to an embodiment.

Meanwhile, in the biomolecule detection apparatus 200 of FIG. 10 that further includes the nanochannel 212, in addition to the third electrode 123 disposed near the nanopore 211, an additional electrode may be further disposed near the nanochannel 212. FIG. 13 is a schematic conceptual view of a structure of a biomolecule detection apparatus 200" that further includes an electrode near the nanochannel 212 according to another embodiment.

Referring to FIG. 13, the biomolecule detection apparatus 200" is different from the biomolecule detection apparatus 200 of FIG. 10 in that the biomolecule detection apparatus 200" includes the fourth electrode 124 between the first electrode 121 and the third electrode 123 near an entrance of the nanochannel 212. That is, the power supply unit 120 of the biomolecule detection apparatus 200" may include the first electrode 121 electrically connected to the sample liquid solution 10 disposed in the front of the nanopore device 210, the second electrode 122 disposed inside the reservoir 101 and electrically connected to the electrolyte 105, the third electrode 123 disposed in an entrance of the nanopore 211, and the fourth electrode 124 disposed near the entrance of the nanochannel 212. The additional fourth electrode 124 may be disposed around the top surface 213 of the nanochannel 212. For example, the fourth electrode 124 may be attached onto the top surface 213 of the nanochannel 212, may be disposed facing the top surface 213 of the nanochannel 212 and separated by a predetermined space, or may be disposed inside the nanochannel 212. Also, as described with reference to FIG. 9, the fourth electrode 124 may be disposed facing the third electrode 123 with respect to the nanopore 211. Other features and functions of the biomolecule detection apparatus 200" of FIG. 13 may be the same as described with reference to the biomolecule detection apparatus 200 of FIG. 10.

In the embodiment of FIG. 13, when an electric potential of the first electrode 121 is 0, an electric potential of the fourth electrode 124 disposed near the entrance of the nanochannel 212 is V1, an electric potential of the third electrode 123 disposed in an entrance of the nanopore 211 is V1+V2, and an electric potential of the second electrode 122 is V1+V2+V3, which may steadily increase. That is, a difference in the electric potential between the first electrode 121 and the third electrode 123 may be greater than that between the first electrode 121 and the fourth electrode 124, and a difference in the electric potential between the first electrode 121 and the second electrode 122 may be further greater than that between the first electrode 121 and the third electrode 123. Accordingly, a relatively uniform voltage drop occurs between the first electrode 121 and the fourth electrode 124 and between the fourth electrode 124 and the third electrode 123, and thus an electric field may be uniformly distributed over a wide range from the first electrode 121 to the nanopore 211 through the nanochannel 212. As a result, the target biomolecules 11 included in the sample liquid solution 10 disposed on the nanopore device 210 may be more easily induced to the nanopore 211.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A biomolecule detection apparatus comprising:
   a nanopore device having a front surface and a rear surface and including a nanopore having a nano-sized diameter;
   a reservoir disposed adjacent to the rear surface of the nanopore device; and
   a power supply unit comprising
      a first electrode positioned in front of the nanopore device;
      a second electrode disposed inside the reservoir, wherein the nanopore device is positioned between the first and second electrodes; and a third electrode disposed between the first electrode and the second electrode on the front surface of the nanopore device adjacent to the nanopore, wherein the nanopore connects the front and the rear surfaces of the nanopore device, and is connected to the reservoir, and wherein the power supply unit is configured to provide voltage signals to the first electrode, the second electrode and the third electrode to produce an electric field that induces target biomolecules contained in a sample proximal the front surface of the nanopore device to pass through the nanopore into the reservoir.

2. The biomolecule detection apparatus of claim 1, wherein the first electrode is positioned to contact a sample liquid solution deposited on the front surface of the nanopore device, and the second electrode is positioned to contact an electrolyte solution contained in the reservoir.

3. The biomolecule detection apparatus of claim 1, wherein the first electrode has negative electric potential or is grounded, and the second electrode and the third electrode have positive electric potentials.

4. The biomolecule detection apparatus of claim 3, wherein a difference in electric potential between the first electrode and the second electrode is greater than a difference in electric potential between the first electrode and the third electrode.

5. The biomolecule detection apparatus of claim 1, wherein the third electrode is ring-shaped and surrounds a perimeter of the nanopore.

6. A biomolecule detection apparatus comprising:
   a nanopore device having a front surface and a rear surface and including a nanopore having a nano-sized diameter;
   a reservoir disposed adjacent to the rear surface of the nanopore device; and
   a power supply unit comprising
      a first electrode positioned in front of the nanopore device;
      a second electrode disposed inside the reservoir, wherein the nanopore device is positioned between the first and second electrodes; and
      a third electrode disposed facing the front surface of the nanopore device between the first electrode and the second electrode, separated from the front surface of the nanopore device by a space, wherein small changes in current that occur between the first and second electrodes when target biomolecules pass through the nanopore are sensed and used to detect and analyze said target biomolecule, wherein said first and second electrodes produce said electric field.

7. The biomolecule detection apparatus of claim 6, wherein the space between the third electrode and the front surface of the nanopore device is less than about 10 µm.

8. The biomolecule detection apparatus of claim 1, wherein the power supply unit further comprises a fourth electrode disposed between the first electrode and the third electrode.

9. The biomolecule detection apparatus of claim 8, wherein at least one of the third electrode or the fourth electrode comprises a plurality of electrode layers.

10. The biomolecule detection apparatus of claim 8, wherein a difference in electric potential between the first electrode and the third electrode is greater than a difference in electric potential between the first electrode and the fourth electrode, and a difference in electric potential between the first electrode and the second electrode is greater than a difference in electric potential between the first electrode and the third electrode.

11. The biomolecule detection apparatus of claim 1, wherein the power supply unit further comprises a fourth electrode disposed facing the third electrode with respect to the nanopore.

12. The biomolecule detection apparatus of claim 1, wherein the nanopore device further comprises a nanochannel in the front surface of the nanopore device, the nanochannel being connected to the nanopore and having a channel diameter greater than the nanopore.

13. The biomolecule detection apparatus of claim 12, wherein the nanochannel and the nanopore share a common central axis and the nanochannel extends in an axial direction from the nanopore.

14. The biomolecule detection apparatus of claim 12, wherein the nanochannel extends generally perpendicular to a central axis of the nanopore such that a sample liquid solution within the nanochannel moves generally perpendicularly to the central axis.

15. The biomolecule detection apparatus of claim 12, wherein the third electrode is disposed on a surface of the nanochannel.

16. The biomolecule detection apparatus of claim 12, wherein the power supply unit further comprises a fourth electrode disposed adjacent to the nanopore between the first electrode and the third electrode.

17. A biomolecule detection apparatus comprising:
   a nanopore device having a front surface and a rear surface and including a nanopore having a nano-sized diameter;
   a reservoir disposed adjacent to the rear surface of the nanopore device; and
   a power supply unit comprising
      a first electrode positioned in front of the nanopore device;
      a second electrode disposed inside the reservoir, wherein the nanopore device is positioned between the first and second electrodes; and
      a third electrode disposed external to the nanopore and adjacent to the nanopore between the first electrode and the second electrode;
      a fourth electrode disposed adjacent to the nanopore between the first electrode and the third electrode, wherein the nanopore connects the front and the rear surfaces of the nanopore device, and is connected to the reservoir, and wherein the power supply unit is configured to provide voltage signals to the first electrode, the second electrode and the third electrode to produce an electric field that induces target biomolecules contained in a sample proximal the front surface of the nanopore device to pass through the nanopore into the reservoir;
   wherein the nanopore device further comprises a nanochannel in the front surface of the nanopore device, the nanochannel being connected to the nanopore and having a channel diameter greater than the nanopore;
   wherein the fourth electrode is disposed inside the nanochannel.

18. The biomolecule detection apparatus of claim 16, wherein a difference in electric potential between the first electrode and the third electrode is greater than a difference in electric potential between the first electrode and the fourth electrode, and a difference in electric potential between the first electrode and the second electrode is greater than a difference in electric potential between the first electrode and the third electrode.

19. The biomolecule detection apparatus of claim 12, wherein the power supply unit further comprises a fourth electrode disposed facing the third electrode such that the nanopore is disposed between the fourth and third electrodes.

20. The biomolecule detection apparatus of claim 19, wherein the fourth electrode is disposed on the front surface of the nanopore device.

21. A method of detecting a biomolecule comprising applying a sample containing a target biomolecule to the front surface of a biomolecule detection apparatus comprising:

- a nanopore device having a front surface and a rear surface and including a nanopore having a nano-sized diameter;
- a reservoir disposed adjacent to the rear surface of the nanopore device; and
- a power supply unit comprising
  - a first electrode positioned in front of the nanopore device;
  - a second electrode disposed inside the reservoir, wherein the nanopore device is positioned between the first and second electrodes; and
  - a third electrode disposed external to the nanopore and adjacent to the nanopore between the first electrode and the second electrode;

applying an electric field to the nanopore of the biomolecule detection apparatus, whereby the target biomolecule is transported through the nanopore of the biomolecule detection apparatus; and detecting and analyzing the target biomolecules by sensing a change in current between the first and second electrodes of the biomolecule detection device, wherein said electrodes are used to apply said electric field, wherein a change in current indicates the passage of the target biomolecule through the nanopore.

22. The method of claim 21, wherein the biomolecule is DNA or RNA.

23. The method of claim 21, wherein the power supply unit further comprises a fourth electrode disposed facing the third electrode such that the nanopore is disposed between the fourth and third electrodes.

* * * * *